United States Patent

Nagata et al.

[11] Patent Number: 5,945,568
[45] Date of Patent: Aug. 31, 1999

[54] METHOD FOR PRODUCING A GLYCOL ETHER

[75] Inventors: Koichi Nagata; Toshiyuki Furuya, both of Yokkaichi, Japan

[73] Assignee: Mitsubishi Chemical Corporation, Tokyo, Japan

[21] Appl. No.: 08/864,412

[22] Filed: May 28, 1997

[30] Foreign Application Priority Data

May 29, 1996 [JP] Japan .................................. 8-134956

[51] Int. Cl.⁶ .................................................. C07C 43/11
[52] U.S. Cl. ........................................ 568/618; 568/620
[58] Field of Search .................................... 568/618, 620, 568/605, 599

[56] References Cited

U.S. PATENT DOCUMENTS

| | | |
|---|---|---|
| 2,053,708 | 9/1936 | Fife . |
| 2,717,137 | 8/1955 | Patton . |
| 2,902,478 | 9/1959 | Anderson . |
| 3,317,508 | 5/1967 | Winquist . |
| 3,919,126 | 11/1975 | Rakshys, Jr. et al. . |
| 4,360,698 | 11/1982 | Sedon . |
| 4,446,313 | 5/1984 | Dix . |
| 5,354,896 | 10/1994 | Pike et al. . |

FOREIGN PATENT DOCUMENTS

| | | |
|---|---|---|
| 0 189 247 | 7/1986 | European Pat. Off. . |
| 0189247 | 7/1986 | European Pat. Off. . |
| 0 212 820 | 3/1987 | European Pat. Off. . |
| 0 250 168 | 12/1987 | European Pat. Off. . |

OTHER PUBLICATIONS

Derwent Abstract, AN 95 340 223, JP 07 233 111, Sep. 05, 1995.

Derwent Abstract, AN 93 112 110, JP 05 049 949, Mar. 02, 1993.

*Primary Examiner*—Gary Geist
*Assistant Examiner*—Jean F. Vollano
*Attorney, Agent, or Firm*—Oblon, Spivak, McClelland, Maier & Neustadt, P.C.

[57] ABSTRACT

A method for producing a glycol ether, which can maintain a high catalyst-activity and high productivity, can control reaction-selectivity and which comprises reacting an alkylene oxide with an alcohol in the presence of a catalyst, wherein the catalyst is an anion exchange resin which comprises, as the substrate, a polymer of a vinyl aromatic compound and which has a structure such that a quaternary ammonium group is bonded to the aromatic group via a linking group having a chain length of at least 3.

11 Claims, No Drawings

METHOD FOR PRODUCING A GLYCOL ETHER

BACKGROUND OF THE INVENTION

1. Field of the Invention

The present invention relates to a method for producing a glycol ether. Particularly, the present invention relates to a method for producing a glycol ether, which comprises reacting an alkylene oxide with an alcohol in the presence of a catalyst.

2. Discussion of Background

Glycol ethers are useful as solvents for paints or inks, as components to be incorporated into brake fluids or as intermediates for producing glycol ether acetates. They are produced usually by reacting alkylene oxides with alcohols in the presence of homogeneous base catalysts such as alkali-metal hydroxides or amines (see the following reaction schemes (i) and (ii)).

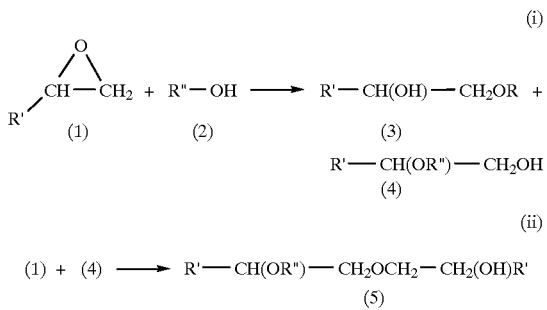

Among compounds formed by the reactions (i) and (ii), the most commercially valuable compound is usually the terminal-adduct (3). However, when the above homogeneous base catalyst is employed, there is a drawback that an adduct having at least 2 mol of an alkylene oxide added, as shown by the formula (5), is likely to form. Further, it is generally difficult to remove the homogeneous catalyst from the system in the purification process. In a case where an asymmetrical alkylene oxide such as propylene oxide is employed, there is a problem such that it is difficult to control the positional selectivity of the reaction and to preferentially obtain the desired terminal adduct (3).

Further, the internal adduct (4) which is a position isomer of the terminal adduct (3), to be formed by the above reactions might possibly show toxicity, and its separation and removal will be required, so that the yield of the terminal adduct tends to be low, and the number of process steps increases, such being undesirable from the economical viewpoint.

To solve such problems, some methods have been proposed for producing glycol ethers by using solid bases as catalysts.

For example, Japanese PCT Publication JP-A-5-503946 discloses a method for producing glycol ethers, wherein an anionic double hydroxide is used as a catalyst.

Further, Japanese Unexamined Patent Publication JP-A-61-204142 discloses a method for producing glycol ethers, wherein an anion exchange resin containing a primary, secondary or tertiary amino group or a secondary or tertiary amino group having a substituent, is used as the catalyst. In an Example of this publication, it is disclosed that when propylene oxide and ethanol were reacted glycol ether was formed at a conversion of 85%.

However, such anion exchange resins generally had a problem in the life of the catalysts, since their heat stability is low as compared with cation exchange resins, and their durability was accordingly poor.

The present inventors have conducted extensive studies taking the above described related art into consideration and as a result, have found that by employing an anion exchange resin having a certain specific structure as the catalyst, not only the problem with respect to the durability of the catalyst can be solved, but also it is possible to produce glycol ethers having a terminal-adduct type structure at high reactivity and selectivity. The present invention has been accomplished on the basis of this discovery.

SUMMARY OF THE INVENTION

Thus, the present invention provides a method for producing a glycol ether, which comprises reacting an alkylene oxide with an alcohol in the presence of a catalyst, wherein the catalyst is an anion exchange resin which comprises, as the substrate, a polymer of a vinyl aromatic compound and which has a structure such that a quaternary ammonium group is bonded to the aromatic group via a linking group having a chain length of at least 3.

DETAILED DESCRIPTION OF THE PREFERRED EMBODIMENTS

Now, the method of the present invention will be described in detail.

In the present invention, an anion exchange resin which comprises, as the substrate, a polymer of a vinyl aromatic compound and which has a structure such that a quaternary ammonium group is bonded to the aromatic group via a linking group having a chain length of at least 3, is used as the catalyst. The monomer constituting the substrate of the anion exchange resin may, for example, be styrene, vinyl toluene, ethylvinyl benzene or vinyl naphthalene. The linking group which links the quaternary ammonium group to the aromatic group of the substrate is not particularly limited so long as its chain length is at least 3, and it may, for example, be an alkylene group or an alkyleneoxyalkylene group.

Here, the chain length is meant for the number of atoms of the linking moiety of the group for linking the quaternary ammonium group to the aromatic group. For example, in the case of straight chain alkylene group (a polymethylene group), its carbon number represents the chain length.

The resin having a linking group with a chain length of 2 is very poor in the durability as a catalyst, since degradation of the resin during use at a high temperature is substantial. Likewise, a resin having a linking group with a chain length of 1 does not provide a sufficiently high conversion of an alkylene oxide, and its durability as a catalyst is also inadequate.

An anion exchange resin can be prepared usually by polymerizing a vinyl aromatic compound (hereinafter referred to as a precursor monomer) having a corresponding structure with a substitution-able group such as a tosyl group or a halogen atom such as chlorine, bromine or iodine, if necessary together with other monomer, and then introducing a quaternary ammonium group to the substitution-able group position.

As an example of a suitable anion exchange resin to be used in the present invention, an anion exchange resin having a structural unit having a quaternary ammonium group, represented by the following formula (I) may be mentioned:

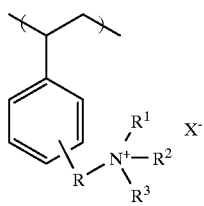 (I)

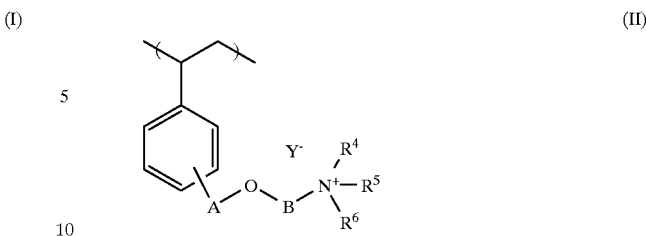 (II)

where R is an alkylene group having a chain length of from 3 to 10, said alkylene group may have a cyclic hydrocarbon group in its chain, or may have an alkyl group as a substituent, each of $R^1$ to $R^3$ is a $C_{1-4}$ alkyl group or a $C_{1-4}$ alkanol group, $X^-$ is an anion, and the benzene ring may be substituted by an alkyl group or a halogen atom, and may be condensed with other aromatic ring.

The chain length of the alkylene group R in the above formula (I) is from 3 to 10, preferably from 3 to 6. Such an alkylene group may contain a cyclic hydrocarbon group in its chain, or may be substituted by an alkyl group.

Specific examples of such an alkylene group (hereinafter "n-alkylene group" means a straight chain alkylene group (a polymethylene group) having a free valence at each end, and an alkyl group represents a methyl group or an ethyl group) include a n-propylene group, a 1-alkyl-n-propylene group, a 2-alkyl-n-propylene group, a 3-alkyl-n-propylene group, a n-butylene group, a 1-alkyl-n-butylene group, a 2-alkyl-n-butylene group, a 3-alkyl-n-butylene group, a 4-alkyl-n-butylene group, a n-pentylene group, a 1-alkyl-n-pentylene group, a 2-alkyl-n-pentylene group, a 3-alkyl-n-pentylene group, a 4-alkyl-n-pentylene group, a 5-alkyl-n-pentylene group, a n-hexylene group, a 1-alkyl-n-henxylene group, a 2-alkyl-n-hexylene groups a 3-alkyl-n-hexylene group, a 4-alkyl-n-hexylene group, a 5-alkyl-n-hexylene group, a 6-alkyl-n-hexylene group, a 2,4-dialkyl-n-pentylene group, a 2,4-dialkyl-n-hexylene group, a 2,5-dialkyl-n-hexylene group, and a 3,5-dialkyl-n-hexylene group.

Each of $R^1$ to $R^3$ is a $C_{1-4}$ alkyl group or a $C_{1-4}$ alkanol group. Specific examples thereof include a methyl group, an ethyl group, a n-propyl group, an i-propyl group, a n-butyl group, a s-butyl group, a t-butyl group, an i-butyl group, a 2-hydroxyethyl group, a 3-hydroxypropyl group, and a 4-hydroxybutyl group.

$X^-$ represents an anion. Specific examples include a hydroxyl ion and a halogen ion such as a chlorine ion, a bromine ion or an iodine ion. Further, the benzene ring may be substituted by a $C_{1-4}$ alkyl group or a halogen atom. Further, it may be condensed with other aromatic ring to form a condensed aromatic ring such as a naphthalene ring or an anthracene ring.

As another preferred example of an anion exchange resin, an anion exchange resin having a structural unit having a quaternary ammonium group, represented by the following formula (II), may be mentioned.

wherein A is a $C_{1-4}$ alkylene group, B is a $C_{1-8}$ alkylene group, and each of A and B may have an alkyl group as a substituent, each of $R^4$ to $R^6$ is a $C_{1-4}$ alkyl group or a $C_{1-4}$ alkanol group, $Y^-$ represents an anion, and the benzene ring may be substituted by an alkyl group or a halogen atom and may be condensed with other aromatic ring.

In the above formula (II), A is a $C_{1-4}$ alkylene group and B is a $C_{1-8}$, preferably $C_{4-8}$, alkylene group. Each of such alkylene groups may be substituted by an alkyl group. Specific examples of such alkylene groups may be the same as exemplified for the alkylene group R in the above formula (I) in addition to a methylene group and an ethylene group. Each of $R^4$ to $R^6$ is a $C_{1-4}$ alkyl group or a $C_{1-4}$ alkanol group, and specific examples thereof may be the same as exemplified for the groups $R^1$ to $R^3$ in the above formula (I). Further, anion $Y^-$ may be the same as exemplified for $X^-$. Likewise, the benzene ring may be substituted by an alkyl group or a halogen atom and may be condensed with other aromatic ring.

The above-mentioned anion exchange resin having a structural unit having a quaternary ammonium group is preferably a cross-linked polymer. Such a cross-linked polymer can be prepared by copolymerizing e.g. the above-mentioned precursor monomer with an unsaturated hydrocarbon group-containing crosslinkable monomer, if necessary, together with other monomer, followed by introducing a quaternary ammonium group.

As such an unsaturated hydrocarbon group-containing crosslinkable monomer, divinyl benzene, divinyl toluene, divinyl naphthalene or ethylene glycol dimethacrylate may, for example, be mentioned. Among them, divinyl benzene is preferred.

Japanese Unexamined Patent Publication JP-A-5-49949 discloses that the specific anion exchange resin containing a structural unit having a quaternary ammonium group, corresponding to the above formula (I) and a structural unit derived from an unsaturated hydrocarbon group-containing crosslinkable monomer, has excellent heat resistance as an anion exchanger useful for a process for producing extra pure water.

The present inventors have found that such an anion exchange resin has excellent properties such that when it is used as a catalyst for a reaction of an alkylene oxide with an alcohol to produce a glycol ether, it shows not only excellent heat resistance but also high catalytic activities and position selectivity when asymmetrical alkylene oxide is used.

In the method of the present invention, by employing the anion exchange resin having the above specified quaternary ammonium group, as a catalyst, an alkylene oxide and an alcohol are reacted to form a glycol ether.

The alkylene oxide may be an aliphatic alkylene oxide such as ethylene oxide or propylene oxide, or an aromatic alkylene oxide such as styrene oxide. Particularly preferred is ethylene oxide or propylene oxide.

The alcohol may, for example, be an aliphatic monohydric alcohol such as methanol, ethanol or propanol, an aliphatic dihydric alcohol such as ethylene glycol or propylene glycol, or a phenol such as phenol or methylphenol. Particularly preferred is a $C_{1-6}$ aliphatic monohydric alcohol.

The reaction system may be a batch system a semibatch system or a continuous system In any system it is important to sufficiently contact the reaction substrate with the catalyst. For this purpose, it is important to select, for example, a suitable agitating method in the batch system, or a suitable flow rate in the continuous system.

The molar ratio of the alcohol to the alkylene oxide in the starting material is usually within a range of from 2/1 to 10/1, preferably from 3/1 to 7/1. If the proportion of the alcohol is less than this range, selectivity for a 1:1 adduct of the alcohol and the alkylene oxide tends to be low, or heat removal from the reaction system tends to be difficult. On the other hand, if the proportion of the alcohol exceeds the above range, a large amount of energy tends to be required for separating the alcohol from the product in the subsequent purification step.

The reaction temperature is usually from 50° to 200° C., preferably from 60° to 120° C. The reaction pressure is usually from 1 to 50 kgf/cm$^2$, preferably from 2 to 20 kgf/cm$^2$.

Now, practical embodiments of the present invention will be specifically described with reference to Examples. However, it should be understood that the present invention is by no means restricted by such specific Examples. Further in the Tables, "E1", "C3" or the like represent "Example 1", "Comparative Example 3" or the likes respectively.

EXAMPLE 1

Using an anion exchange resin (hereinafter referred to as "RIE-1") comprising a structural unit having a quaternary ammonium group, represented by the following formula (6) and a structural unit derived from an unsaturated hydrocarbon group-containing crosslinkable monomer, as a catalyst, propylene oxide and methanol were reacted to produce propylene glycol monomethyl ethers Further, the properties of RIE-1 are shown in Table 1.

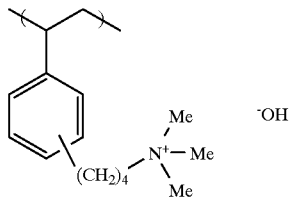

(6)

100 cc of RIE-1 was packed in a tubular packed bed reactor, and a mixed solution of methanol and propylene oxide (molar ratio: 5/1) was passed therethrough under a pressure of 3.0 kgf/cm$^2$ at a temperature of 82° C. so that the residence time (superficial velocity base) at the catalyst layer would be one hours. The effluent was analyzed by gas chromatography, whereby the conversion of propylene oxide was 99%, and the proportion of the 1:1 adduct of methanol and propylene oxide in the product was 98% (95% thereof was the terminal adduct i.e. 1-methoxy-2-propanol). Upon expiration of one month, the catalytic properties were maintained, and there was no substantial change in the conversion and selectivity. The analytical values of the effluent upon expiration of one day and upon expiration of one month are shown in Table 2-1, and the water content and the ion exchange capacity of the anion exchange resin (RIE-1) upon expiration of one month are also shown in Table 1.

EXAMPLE 2

The reaction was carried out under the same conditions as in Example 1 except that the catalyst was changed to an anion exchange resin (hereinafter referred to as "RIE-2") comprising a structural unit having a quaternary ammonium group, represented by the following formula (7) and a structural unit derived from an unsaturated hydrocarbon group-containing crosslinkable monomer. The properties of RIE-2 are shown in Table 1.

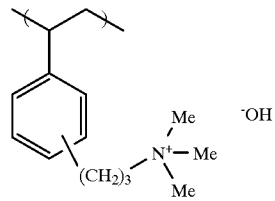

(7)

By the gas chromatography analysis of the effluent immediately after initiation of the reaction, the conversion of propylene oxide was 98%, and the proportion of the 1:1 adduct of methanol and propylene oxide in the product was 98% (95% thereof was 1-methoxy-2-propanol). Upon expiration of one month, the catalytic properties were maintained, and no substantial change was observed in the conversion and selectivity The analytical values of the effluent upon expiration of one day and upon expiration of one month are shown in Table 2-1, and the water content and the ion exchange capacity of the ion exchange resin (RIE-2) upon expiration of one month are shown in Table 1.

EXAMPLE 3

The reaction was carried out under the same conditions as in Example 1 except that the catalyst was changed to an anion exchange resin (RIE-3) comprising a structural unit having a quaternary ammonium group, represented by the following formula (8) and a structural unit derived from an unsaturated hydrocarbon group-containing crosslinkable monomer. The properties of RIE-3 are shown in Table 1.

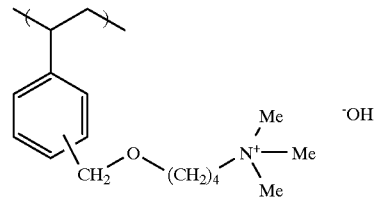

(8)

By the gas chromatography analysis of the effluent immediately after initiation of the reaction, the conversion of propylene oxide was 97%, and the proportion of the 1:1 adduct of methanol and propylene oxide in the product was 98% (95% thereof was 1-methoxy-2-propanol). Upon expiration of one month, the catalytic properties were maintained, and no substantial change was observed in the conversion and selectivity. The analytical values of the effluent upon expiration of one day and upon expiration of one month are shown in Table 2-1 and the water content and the ion exchange capacity of the ion exchange resin (RIE-3) upon expiration of one month are shown in Table 1.

EXAMPLE 4

Using the same anion exchange resin RIE-1 as used in Example 1, as a catalyst, ethylene oxide and butanol were reacted to obtain ethylene glycol monobutyl ether.

100 cc of RIE-1 was packed in a tubular packed bed reactor, and a mixed liquid of butanol and ethylene oxide (molar ratio: 2.6/1) was passed therethrough under a pressure of 15.0 kgf/cm$^2$ at a temperature of 80° C. so that the residence time (superficial velocity base) at the catalyst layer would be 30 minutes. The effluent was analyzed by gas chromatography, whereby the conversion of ethylene oxide was 99%, and the proportion of the 1:1 adduct of butanol and ethylene oxide in the effluent was 72%. Upon expiration of one month, the catalytic properties were maintained, and no substantial change was observed in the conversion and the selectivity. The analytical values of the effluent upon expiration of one day and upon expiration of one month are shown in Table 2-2, and the water content and the ion exchange capacity of the ion exchange resin RIE-1 upon expiration of one month are also shown in Table 1.

COMPARATIVE EXAMPLE 1

The reaction was carried out under the the same conditions as in Example 1 except that the catalyst was changed to a commercially available anion exchange resin (Diaion SA-10A, tradename, manufactured by Mitsubishi Chemical Corporation). The above "SA-10A" is an anion exchange resin having a structural unit having a quaternary ammonium group, represented by the following formula (9).

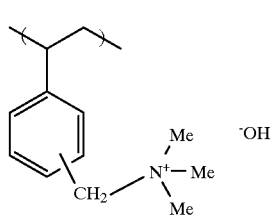

(9)

The difference in the structure between "SA-10A" and the ion exchange resin (RIE-1) used in Example 1 was that the chain length (carbon number) of the alkylene group between the benzene ring and the nitrogen atom, is 4 in RIE-1, whereas the chain length is 1 in "SA-10A". General properties of "SA-10A" are shown in Table 1.

By the gas chromatography analysis of the effluent immediately after initiation of the reaction, the conversion of propylene oxide was 95%, and the proportion of the 1:1 adduct of methanol and propylene oxide in the product was 98% (94% thereof was 1-methoxy-2-propanol). Upon expiration of two weeks after initiation of the reactions the conversion decreased to 60%.

The analytical values of the effluent upon expiration of one day and upon expiration of two weeks are shown in Table 2-1, and the water content and the ion exchange capacity of the anion exchange resin (SA-10A) upon expiration of two weeks are shown in Table 1.

COMPARATIVE EXAMPLE 2

The reaction was carried out under the the same conditions as in Example 1 except that the catalyst was changed to a commercially available anion exchange resin (Diaion WA-10, tradename, manufactured by Mitsubishi Chemical Corporation). The above "WA-10" is an anion exchange resin having a structural unit having a tertiary amino group i.e. not a quaternary ammonium group. The general properties of "WA-10" are shown in Table 1.

By the gas chromatography analysis of the effluent immediately after initiation of the reactions the conversion of propylene oxide was 90%, and the proportion of the 1:1 adduct of methanol and propylene oxide in the product was 95% (94% thereof was 1-methoxy-2-propanol). Upon expiration of two weeks after initiation of the reaction, the conversion decreased to 59%.

The analytical values of the effluent upon expiration of one day and upon expiration of two weeks are shown in Table 2-1, and the water content and the ion exchange capacity of the anion exchange resin (WA-10) upon expiration of two weeks are shown in Table 1.

COMPARATIVE EXAMPLE 3

The reaction was carried out in the the same conditions as in Example 1 except that the catalyst was changed to a sodium hydroxide. The concentration of the catalyst was 100 ppm, and the reaction temperature was 100° C.

By the gas chromatography analysis of the effluent immediately after initiation of the reactions the conversion of propylene oxide was 99%, and the proportion of the 1:1 adduct of methanol and propylene oxide in the product was 93% (91% thereof was 1-methoxy-2-propanol). The analytical values of the effluent at the initial stage are shown in Table 2-1.

COMPARATIVE EXAMPLE 4

The reaction of ethylene oxide with butanol was carried out under the same reaction conditions as in Example 4 except that the catalyst was changed to the same commercially available ion exchange resin (Diaion SA-10A, tradename, manufactured by Mitsubishi Chemical Corporation) as used in Comparative Example 1.

By the gas chromatography analysis of the effluent immediately after initiation of the reaction, the conversion of ethylene oxide was 96%, and the proportion of the 1:1 adduct of butanol and ethylene oxide was 71%. Upon expiration of three weeks after initiation of the reaction, the conversion decreased to 80%. The analytical values of the effluent upon expiration of one day and upon expiration of three weeks are shown in Table 2-2, and the water content and the ion exchange capacity of the ion exchange resin SA-10A upon expiration of three weeks are shown in Table 1.

COMPARATIVE EXAMPLE 5

The reaction in Example 4 was carried out by changing the catalyst to sodium hydroxide. The concentration of the catalyst was 100 ppm, and the reaction temperature was 100° C., and other conditions were the same as in Example 4.

By the gas chromatography analysis of the effluent immediately after initiation of the reaction, the conversion of ethylene oxide was 99%, and the proportion of the 1:1 adduct of butanol and ethylene oxide in the effluent was 61%. The analytical values of the initial components are shown in Table 2-2.

A summary of these test results is shown in Table 3. As is apparent from this table, when the method of the present invention is used, the durability of the catalyst will be improved, and it is possible to produce a glycol ether having a terminal adduct structure having a high commercial value at high selectivity and with high catalyst activities. Further, formation of the by-product (the internal adduct) can be suppressed, whereby cost for purification of the product can be reduced.

TABLE 1

Properties of ion exchange resin

| Resin No. | Test No. | Chain length | Physical nature | Particle size (mm) | Initial Water content (%) | Initial IE capacity (eq/l) | Number of days | After use Water content (%) | After use IE capacity (eq/l) |
|---|---|---|---|---|---|---|---|---|---|
| RIE-1 | E1 | 4 | Pale yellow particles | 0.4–0.8 | 51.1 | 1.26 | 30 | 53.8 | 1.09 |
| RIE-2 | E2 | 3 | Pale yellow particles | 0.4–0.8 | 50.3 | 1.31 | 30 | 52.1 | 1.10 |
| RIE-3 | E3 | 6 | Pale yellow particles | 0.4–1.0 | 50.9 | 1.02 | 30 | 52.9 | 0.74 |
| RIE-1 | E4 | 4 | Pale yellow particles | 0.4–0.8 | 51.1 | 1.26 | 30 | 54.5 | 1.04 |
| SA-10A | C1 | 1 | Pale yellow particles | 0.4–0.6 | 46.8 | 1.32 | 14 | 50.3 | 0.91 |
| WA-10 (Amino group type) | C2 | — | Pale yellow particles | 0.3–0.6 | 65.5 | 1.24 | 14 | 67.7 | 0.82 |
| SA-10A | C4 | 1 | Pale yellow particles | 0.4-0.6 | 46.8 | 1.32 | 21 | 50.5 | 0.99 |

Notes: IE capacity: Equivalent of ion exchangeable per unit volume of ion-exchange resin

TABLE 2-1

Reaction results

| Test No. | Catalyst | Number of days for reaction | AO | R"OH | Terminal adduct | Internal adduct | 2 mol addition | AO conversion (%) | Selectivity for terminal adduct (%) |
|---|---|---|---|---|---|---|---|---|---|
|  |  |  | PO | MeOH | PM | 2MlP | DPM |  |  |
| E1 | RIE-1 | 1 | 0.2 | 59.1 | 37.9 | 2.0 | 0.8 | 99 | 93 |
|  |  | 30 | 0.2 | 59.2 | 37.8 | 2.0 | 0.8 | 99 | 93 |
| E2 | RIE-2 | 1 | 0.4 | 59.3 | 37.5 | 2.0 | 0.8 | 98 | 93 |
|  |  | 30 | 0.5 | 59.2 | 37.3 | 2.0 | 0.8 | 98 | 93 |
| E3 | RIE-3 | 1 | 0.7 | 59.4 | 37.1 | 2.0 | 0.8 | 97 | 93 |
|  |  | 30 | 0.7 | 59.3 | 37.2 | 2.0 | 0.8 | 97 | 93 |
| C1 | SA-10A | 1 | 1.3 | 59.6 | 36.0 | 2.2 | 0.8 | 95 | 92 |
|  |  | 14 | 10.6 | 64.8 | 22.4 | 1.4 | 0.8 | 60 | 92 |
| C2 | WA-10 | 1 | 2.6 | 60.6 | 33.0 | 2.0 | 1.8 | 90 | 89 |
|  |  | 14 | 10.9 | 65.2 | 20.7 | 1.3 | 2.0 | 59 | 89 |
| C3 | NaOH | 1 | 0.2 | 59.4 | 34.4 | 3.3 | 2.7 | 99 | 85 |

Notes:
AO: Alkylene oxide, PO: Propylene oxide, MeOH: Methanol, PM: 1-Methoxy-2-propanol, 2MlP: 2-Methoxy-1-propanol, DPM: Dipropylene glycol monomethyl ether

TABLE 2-2

| Test No. | Catalyst | Number of days for reaction | AO | R"OH | 1 mol addition | 2 mol addition | 3 mol addition | AO conversion (%) | Selectivity for terminal adduct (%) |
|---|---|---|---|---|---|---|---|---|---|
|  |  |  | EO | BuOH | EB | DEB | TEB |  |  |
| E4 | RIE-1 | 1 | 0.2 | 57.5 | 30.5 | 9.8 | 2.0 | 99 | 72 |
|  |  | 30 | 0.2 | 57.4 | 30.5 | 9.8 | 2.0 | 99 | 72 |
| C4 | SA-10A | 1 | 0.7 | 58.1 | 29.3 | 9.9 | 2.0 | 96 | 71 |
|  |  | 21 | 3.6 | 62.2 | 24.0 | 8.6 | 1.6 | 80 | 70 |
| C5 | NaOH | 1 | 0.2 | 59.8 | 24.4 | 10.4 | 5.2 | 99 | 61 |

Notes:
AO: Alkylene oxide, EO: Ethylene oxide, BuOH: Butanol, EB: Ethylene glycol monobutyl ether, DEB: Diethylene glycol monobutyl ether, TEB: Triethylene glycol monobutyl ether

TABLE 3

Summary of test results

| Test No. | Catalyst | Chain length | Initial activities (%) AO conversion | Initial activities (%) Selectivity for terminal adduct | Catalyst durability (Remaining ratio, %) AO conversion | Catalyst durability (Remaining ratio, %) IE capacity |
|---|---|---|---|---|---|---|
| E1 | RIE-1 | 4 | 99 | 93 | 100 | 87 |
| E2 | RIE-2 | 3 | 98 | 93 | 100 | 84 |
| E3 | RIE-3 | 6 | 97 | 93 | 100 | 73 |
| E4 | RIE-1 | 4 | 99 | 72 | 100 | 83 |
| C1 | SA-10A | 1 | 95 | 92 | 63 | 69 |
| C2 | WA-10 | — | 90 | 89 | 66 | 66 |
| C3 | NaOH | — | 99 | 85 | — | — |
| C4 | SA-10A | 1 | 96 | 71 | 83 | 75 |
| C5 | NaOH | — | 99 | 61 | — | — |

*Catalyst durability: Data upon expiration of time/initial data × 100(%)
Selectivity for terminal adduct: Selectivity for 1 mol addition in Example 4 and Comparative Examples 4 and 5

What is claimed is:

1. A method for producing a glycol ether, which comprises reacting an alkylene oxide with an alcohol in the presence of a catalyst, wherein the catalyst is an anion exchange resin which comprises, as the substrate, a polymer of a vinyl aromatic compound and which has a structure such that a quaternary ammonium group is bonded to the aromatic group via a linking group having a chain length of at least 3.

2. The method for producing a glycol ether according to claim 1, wherein the catalyst is an anion exchange resin having a structural unit having a quaternary ammonium group, represented by the following formula (I):

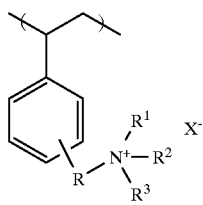

(I)

wherein R is an alkylene group having a chain length of from 3 to 10, each of $R^1$ to $R^3$ is a $C_{1-4}$ alkyl group or a $C_{1-4}$ alkanol group, and $X^-$ is an anion.

3. The method for producing a glycol ether according to claim 1, wherein the catalyst is an anion exchange resin having a structural unit having a quaternary ammonium group, represented by the following formula (II):

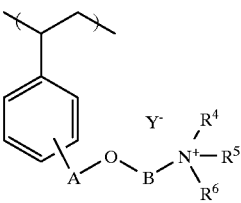

(II)

wherein A is an alkylene group having a chain length of from 1 to 4, B is an alkylene group having a chain length of from 1 to 8, each of $R^4$ to $R^6$ is a $C_{1-4}$ alkyl group or a $C_{1-4}$ alkanol group, and $Y^-$ is an anion.

4. The method for producing a glycol ether according to claim 1, wherein the catalyst is an anion exchange resin having a structural unit having a quaternary ammonium group and a structural unit derived from an unsaturated hydrocarbon group-containing crosslinkable monomer.

5. The method for producing a glycol ether according to claim 1, wherein the alkylene oxide is ethylene oxide or propylene oxide.

6. The method for producing a glycol ether according to claim 1 wherein the alcohol is a $C_{1-6}$ aliphatic monohydric alcohol.

7. The method for producing a glycol ether according to claim 1 wherein the molar ratio of the alcohol to the alkylene oxide is within a range of from 2/1 to 10/1 the reaction temperature is from 50° to 200° C., and the reaction pressure is from 1 to 50 kgf/cm².

8. The method for producing a glycol ether according to claim 2, wherein said alkylene group R is modified by containing a cyclic hydrocarbon group and/or is substituted by an alkyl group, and the benzene ring of the aromatic group is substituted by an alkyl group or halogen or is condensed with at least one other aromatic ring.

9. The method for producing a glycol ether according to claim 3, wherein each of A and B is substituted by alkyl, and the benzene ring of the aromatic group is substituted by an alkyl group or halogen or is condensed with at least one other aromatic ring.

10. The method for producing a glycol ether according to claim 7, wherein said molar ratio ranges from 3/1 to 7/1 said reaction temperature ranges from 60°–120° C. and said pressure ranges from 2–20 kgf/cm².

11. The method for producing a glycol ether according to claim 4, wherein said hydrocarbon group-containing crosslinkable monomer is divinylbenzene, divinyltoluene, divinylnaphthalene or ethylene glycol dimethacrylate.

* * * * *